United States Patent

Frohberger et al.

[11] 3,940,488
[45] Feb. 24, 1976

[54] REPELLENT AMINOALKYLDITHIOCARBAMIC ACIDS

[75] Inventors: Paul-Ernst Frohberger, Leverkusen, Germany; Otto Ewald Urbschat, deceased, late of Cologne-Mulheim, Germany, by Gertrud Emma Maria Gerda Urbschat, administrator; Gunther Hermann, Opladen, Germany

[73] Assignee: Bayer Aktiengesellschaft, Leverkusen, Germany

[22] Filed: Jan. 2, 1975

[21] Appl. No.: 538,427

Related U.S. Application Data

[63] Continuation-in-part of Ser. No. 358,221, May 8, 1973.

[30] Foreign Application Priority Data

May 13, 1972  Germany............................ 2223467

[52] U.S. Cl............................... 424/286; 260/534 S
[51] Int. Cl.²......................................... A01N 9/12
[58] Field of Search .................. 424/286; 260/534 S

[56] References Cited
UNITED STATES PATENTS

3,492,407  1/1970  Anders et al. ...................... 424/315

FOREIGN PATENTS OR APPLICATIONS

1,094,729  6/1961  Germany

OTHER PUBLICATIONS

Chemical Abstracts 72:77963k (1970).

*Primary Examiner*—Leonard Schenkman
*Attorney, Agent, or Firm*—Burgess, Dinklage & Sprung

[57] ABSTRACT

Compositions and methods of using aminoalkyldithiocarbamic acids of the formula

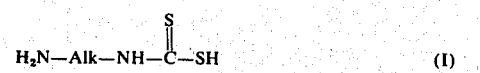

in which
  Alk is an alkylene radical of 2 to 6 carbon atoms,
some of which are new, which possess strong fungicidal and animal-repellent properties.

5 Claims, No Drawings

REPELLENT AMINOALKYLDITHIOCARBAMIC ACIDS

This application is a continuation-in-part of copending application Ser. No. 358,221, filed May 8, 1973.

The present invention relates to and has for its objects the provision of particular new active compositions in the form of mixtures with solid and liquid dispersible carrier vehicles of certain aminoalkyldithiocarbamic acids, some of which are new, and which possess valuable strong fungicidal and animal-repellent properties, and methods for using such compounds in a new way, especially for combating and controlling fungi and animals with other and further objects becoming apparent from a study of the within specification and accompanying examples.

The present invention relates to the use, as fungicides or rodent or ruminant repellents, of certain aminoalkyldithiocarbamic acids, some of which are known.

Some dithiocarbamates in the form of their salts and disulfides have already been known for a long time as fungicides. Heavy metal salts, for example the zinc salts and manganese salts of alkylene-bis-dithiocarbamic acids, have gained especial importance. The salts, for example the zinc salts, of ω-amino-alkyl-dithiocarbamic acids have also already been described as fungicides (see, for example, German Auslegeschriften (German Published Specifications) 1,023,921 and 1,094,729). However, because of their inadequate spectrum of activity, these previously known active compounds can only be used to a limited extent for combating diseases of cereals. Within the framework of the development of new seed dressings against diseases of cereals, which are intended to replace the toxicologically unsafe agents containing mercury, the previously known active compounds based on dithiocarbamate cannot be employed universally, largely because of their lack of activity, or inadequate activity, against species of Helminthosporium.

It is furthermore already known that zinc dimethyl-di-thiocarbamate and tetramethyl-thiuram-disulfide can be used for repelling rodents and ruminants. These two active compounds have gained considerable importance in practice (J. F. Welch, Proceedings Third Vertebrate Pest Conf., San Francisco, 1967, pages 36–40). The action is however not always satisfactory, especially against ruminants.

It has now been found that aminoalkyldithiocarbamic acids of the formula

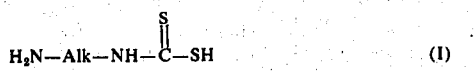

in which

Alk is an alkylene radical of 2 to 6 carbon atoms, are desirable compounds in the combating of pests, for example in agriculture, as they possess strong fungicidal properties and a good repellent action against rodents and ruminants.

One importance of the active compounds resides in their previously unknown fungicidal action against the pathogens of various diseases of cereals, especially against species of Helminthosporium. In view of the previous experience with dithiocarbamate fungicides, the newly discovered effect is particularly surprising. Furthermore, surprisingly, the repellent action of the active compounds is greater than that of the known rodent and ruminant repellents tetramethyl-thiuramdisulfide and zinc-dimethyl-dithiocarbamate. The compounds which can be used according to the invention thus represent an enrichment of the art.

The aminoalkyldithiocarbamic acids to be used according to the invention have been characterized by the formula (I) but they can alternatively be characterized by the formula

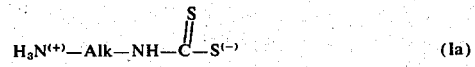

and hereafter when formula (I) is recited it is intended to apply to formula (Ia) as well, unless otherwise expressed.

The following may be mentioned as specific examples of preferred aminoalkyldithiocarbamic acids: 2-aminoethyl-dithiocarbamic acid, 2-aminopropyl-dithiocarbamic acid, 3-aminopropyl-dithiocarbamic acid, 1-aminopropyl-(2)dithiocarbamic acid, 3-aminobutyl-dithiocarbamic acid, 4-aminobutyl-dithiocarbamic acid, 5-aminopentyl-dithiocarbamic acid and 6-aminohexyl-dithiocarbamic acid, especially the ω-aminoalkyldithiocarbamic acids.

Several of the compounds to be used according to the invention are known (see, for example, Ber. 5, 241 (1872); 55, 3351 (1922), Hoppe-Seylers Zeitschrift f. phys. Chem. 180, 202 (1929)). Where they have not been previously described in detail, they can be prepared in accordance with customary processes known from the literature. Thus, they are as a rule obtained by the action of equimolar amounts of carbon disulfide on diaminoalkanes in diluents such as water, alcohols, hydrocarbons or ethers, at normal temperature.

The active compounds to be used according to the invention display a strong fungitoxic action and are distinguished by a broad spectrum of activity. Their low toxicity to warm-blooded animals and their good toleration by higher plants permits them to be used as plant protection agents against fungal diseases. They do not damage crop plants in the concentrations required for combating fungi. Fungitoxic agents in plant protection are employed for combating fungi from the most diverse classes of fungi, such as Archimycetes, Phycomycetes, Ascomycetes, Basidiomycetes and *Fungi Imperfecti*.

Thus they show a good action against seed-borne fungi, such as *Ustilago avenae*, *Fusarium nivale* and Helminthosporium and against soil fungi, such as Rhizoctonia species, Fusarium species, Pythium species, Phytophthora species, *Verticillium alboatrum*, *Thielaviopsis basicola* and *Corticium rolfsii*.

The active compounds are thus particularly suitable for soil treatment and seed dressing.

Furthermore, as already stated, the active compounds according to the invention display a repellent action towards harmful leporine animals and rodents, such as hares and rabbits (Leporidae), as well as sciurids (Sciuroidea), gophers (Geomyoidae) and muroids (Muroidae), with which there are classed essentially the glirids (Muscardinidae) and the mice (Muridae).

The hares and rabbits include, for example, the wild rabbit (*Oryctolagus cuniculus*); the sciurids include, for example, the European souslik (*Citellus citellus*) and the mantled ground squirrel (*Citellus lateralis*); and the gophers include, for example, the mountain pocket gopher (*Thomomys talpoides*). With the glirids there is classed, for example, the fat dormouse (*Glis glis*). The mice comprise essentially among the murines (Murinae) the rats (Rattus spec.), such as the black rat (Rattus rattus) and the Norway rat (*Rattus norvegicus*); the house mice (Mus spec.), such as *Mus musculus*; among the cricetines (Cricetinae) is the European hamster (*Cricetus cricetus*) and among the cricetids (Microtinae), for example, are the common vole (*Microtus arvalis*), the field vole (*Microtus agrestis*) and the water vole (*Arvicola terrestris*).

The substances according to the invention also repel harmful ruminants (Ruminantia), as the most important groups of which there are to be mentioned the deer (Cervidae) and the bovids (Bovidae).

The deer include, for example, the roe deer (Capreolus capreolus), the white-tailed or Virginia deer (Odocoileus spec.), the fallow deer (Dama dama), the wapiti (*Cervus canadensis*) and the red deer (*Cervus elaphus*). The bovids include, among the groups of the rupicaprine animals (Rupicaprinae), especially the sheep (Ovis spec.) and goats (Capra spec.).

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, rodent- or ruminant-repellents, or insecticides, acaricides, rodenticides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

To develop a repellent action, the active compounds to be used according to the invention, their formulations and the application forms prepared therefrom can furthermore be employed in the customary manner, for example again by treatment of seed, by spraying, dusting or sprinkling suitable preparations of active compound onto plants or parts of plants in danger of being eaten by rodents and/or gnawed by ruminants (for example deer gnawing), by soil treatment, by fumigation in chambers or in subterranean structures, by the application of repellent coverings and barriers above ground or below ground, and by impregnation of materials endangered by rodents and/or ruminants, such as wood, paper, rubber and plastics.

Spray liquors or pastes for producing rodent-repellent and ruminant-repellent coatings on, for example, endangered plants or parts of plants, in general contain from 0.1 to 20 per cent by weight of active compound, preferably 0.5 to 10%. Materials which are impregnated with the active compounds should possess an active compound concentration of about 0.1 to 5 per cent by weight in the surface layer.

In the treatment of seed, amounts of active compound of 0.01 g to 10 g per kg of seed, preferably 0.05 to 5 g, are generally required. For the treatment of soil, amounts of active compound of 1 to 500 g per cubic meter of soil, preferably 10 to 200 g, are generally required.

Furthermore, the present invention contemplates methods of selectively killing, combating or controlling pests, e.g. fungi, rodents and ruminants, which comprises applying to at least one of correspondingly (a) such fungi, and (b) the corresponding habitat of such fungi, rodents or ruminants, i.e. the locus to be protected, a correspondingly combative or toxic amount, i.e. a fungicidally, or rodent- or ruminant-repellent effective amount, of the particular active compound of the invention alone or together with a carrier vehicle as noted above. The instant formulations or compositions are applied in the usual manner, for instance by spraying, atomizing, vaporizing, scattering, dusting, watering, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Seed dressing test/stripe disease of barley
(seed-born mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, in moist compost earth in closed Petri dishes, was exposed to a temperature of 4°C for 10 days in a refrigerator. The germination of the barley, and possibly also of the fungus spores, was thereby initiated. Two batches of 50 grains of the pregerminated barley was subsequently sown 2 cm deep in Fruhstorfer standard soil and cultivated in a greenhouse at temperatures of about 18°C in seed boxes which were exposed to light for 16 hours daily. The typical symptoms of the stripe disease developed within 3 to 4 weeks.

After this time, the number of diseased plants was determined as a percentage of the total number of emerged plants.

The fewer plants were diseased, the more effective was the active compound.

The active compounds, the amounts of active compound used and the number of diseased plants can be seen from Table 1.

Table 1

| Active compound | Seed dressing test/stripe disease of barley | | |
| --- | --- | --- | --- |
| | | Amount of active compound used, in mg/kg of seed | Number of plants with stripe disease as % of the total number of emerged plants |
| without dressing | | — | 26.4 |
| $[H_2N-CH_2-CH_2-NH-CS-S]_2Zn$ | | 200 | 15.5 |
| | | 600 | 17.2 |
| (known) | (A) | 1,200 | 9.2 |
| $[(C_2H_5)_2N-(CH_2)_3-NH-CS-S]_2Zn$ | | 200 | 26.8 |
| | | 600 | 17.0 |
| (known) | (B) | 1,200 | 16.0 |
| $NH_2-(CH_2)_4-NH-CS-SH$ | (1) | 200 | 3.0 |
| | | 600 | 0.0 |
| $H_2N-CH_2-CH_2-NH-\overset{\overset{S}{\|}}{C}-SH$ | (2) | 600 | 6.2 |

EXAMPLE 2

Seed dressing test/snow mold
(seed-born mycosis)

To produce a suitable dry dressing, the active compound was extended with a mixture of equal parts by weight of talc and kieselguhr to give a finely powdered mixture with the desired concentration of active compound.

To apply the dressing, rye seed, which was naturally infected by *Fusarium nivale*, was shaken with the dressing in a closed glass flask. Two batches of 100 grains of this seed were sown 1 cm deep in seed boxes containing Fruhstorfer standard soil. The young plants developed in climatic chambers at 10°C, at a relative atmospheric humidity of 95% and in diffused natural light; they showed the typical symptoms of snow mold within the first 3 weeks.

After this time, the number of Fusarium-infected plants was determined as a percentage of the total number of emerged plants. The smaller the number of diseased plants, the more effective was the active compound.

The active compounds, the amounts of active compound used and the number of diseased plants can be seen from Table 2.

Table 2

| Active compound | | Seed dressing test/snow mould Amount of active compound used in mg/kg of seed | Number of Fursarium-infected plants as % of the total number of emerged plants |
|---|---|---|---|
| without dressing | | — | 12.1 |
| [(C$_2$H$_5$)$_2$N—(CH$_2$)$_3$—NH—CS—S—]$_2$Zn (known) | (B) | 600<br>1,200 | 8.6<br>8.2 |
| H$_2$N—(CH$_2$)$_4$—NH—$\overset{\overset{S}{\|\|}}{C}$—SH | (1) | 600<br>1,200 | 0.0<br>0.0 |
| H$_2$N—CH$_2$—CH$_2$—NH—$\overset{\overset{S}{\|\|}}{C}$—SH | (2) | 600<br>1,200 | 1.1<br>0.5 |
| H$_2$N—(CH$_2$)$_6$—NH—$\overset{\overset{S}{\|\|}}{C}$—SH | (3) | 600 | 0.5 |

EXAMPLE 3

Seed dressing test/loose smut of oats (seed-born mycosis)

To produce a suitable dry dressing, the active compound was extended with a mixture of equal parts by weight of talc and kieselguhr to give a finely powdered mixture with the desired concentration of active compound.

To apply the dressing, oat seed, which was naturally infested with loose smut (*Ustilago avenae*), was shaken with the dressing in a closed glass flask. Two batches of 100 grains of the seed were sown 2 cm deep in seed boxes containing a mixture of 1 part by volume of Fruhstorfer standard soil and 1 part by volume of quartz sand. The boxes were placed in a greenhouse at a temperature of about 18°C, kept normally moist and exposed to light for 16 hours daily. After 10 – 12 weeks, the oats flowered and showed healthy and diseased panicles (smutted panicles).

After this time, the number of diseased panicles was determined as a percentage of the total number of developed panicles. 0% means that no diseased panicles were present; 100% means that all the panicles were diseased. The fewer diseased panicles were formed, the more effective was the active compound.

The active compounds, the amounts of active compound used and the number of diseased panicles can be seen from Table 3.

Table 3

| Active compounds | | Seed dressing test/loose smut of oats Active compound concentration in mg/kg of seed | Number of smutted panicles as % of the total of developed panicles |
|---|---|---|---|
| Without dressing | | — | 7.8 |
| (C$_2$H$_5$)$_2$N—CH$_2$—CH$_2$—CH$_2$—NH—$\overset{\overset{S}{\|\|}}{C}$—SH (known from German Offenlegungsschrift (German Published Specification) 1,693,179) | (C) | 900 | 5.3 |
| H$_2$N—CH$_2$—CH$_2$—NH—$\overset{\overset{S}{\|\|}}{C}$—SH | (2) | 900 | 0.0 |
| H$_2$N—(CH$_2$)$_6$—NH—$\overset{\overset{S}{\|\|}}{C}$—SH | (3) | 900 | 0.0 |

EXAMPLE 4

Repellent test/white footed mouse

Test animal: North American white footed mouse (*Peromyscus maniculatus*)

Solvent: Acetone

Concentration of active compound in the test feed: 2%

To produce a suitable preparation of active compound, 2 parts by weight of active compound were dissolved in as small an amount as possible of the abovementioned solvent, this solution was intimately mixed with 98 parts by weight of seed wheat and the solvent was allowed to evaporate.

5 white footed mice kept separately received, in addition to a disliked standard feed, 25 treated wheat grains on each of 3 successive days. The number of grains eaten by each animal was recorded daily.

The measure of the repellent action was the reduction in consumption, that is to say the percentage by which the effective consumption (in per cent of the total amount of wheat offered) was reduced compared to the 100% consumption always to be expected in the case of the untreated wheat. 100% reduction in consumption means that no wheat grains at all were eaten and the repellent action was thus complete. The values quoted comprise the result of the consumption of all test animals during the entire test.

The active compounds, the number of the individual tests and the results can be seen from Table 4:

Table 4

| Active compound | repellent test/white footed mouse | |
|---|---|---|
| | Number of individual tests | Reduction in consumption in % |
| Zinc-dimethyldithio-carbamate (known) (D) | 1 | 31.5 |
| $H_2N-(CH_2)_4-NH-\overset{\overset{S}{\|}}{C}-SH$ (1) | 1 | 62.4 |

Table 5

| Active compound | repellent test/house mouse | |
|---|---|---|
| | Number of individual tests | Repellency in % (average value) |
| Tetramethylthiuram disulphide (known) (E) | 3 | 67.8 |
| $H_2N-(CH_2)_4-NH-\overset{\overset{S}{\|}}{C}-SH$ (1) | 5 | 82.6 |

EXAMPLE 6

In a re-run of Example 5 with a different group of mice the following results were obtained:

Table 6

| Active compound | Number of individual tests | Repellency in % (average Valve) |
|---|---|---|
| $(CH_3)_2N-(CH_2)_3NH-CO-S-C_2H_5 \cdot HCl$ (known from German DOS 1,643,040) | 4 | 42.9 |
| $H_2N-(CH_2)_4-NH-\overset{\overset{S}{\|}}{C}-SH$ (1) | 4 | 61.25 |

EXAMPLE 5

Repellent test/house mouse
Test animal: white laboratory mouse (*Mus musculus*)
Concentration of active compound in the test fodder: 0.5%

To produce an appropriate preparation of the active compound, 3 parts by weight of active compound were mixed with 2.8 parts by weight of highly dispersed silica and 4.2 parts by weight of talc. To prepare the test bait, 1.67 parts by weight of this active compound concentrate were intimately mixed with 95 parts by weight of a meal-like standard feed customary for keeping test animals, with the addition of 3.33 parts by weight of methylcellulose and a little water. Spherical bait pellets were formed from 6 g of dry substance and were dried for 24 hours at room temperature prior to the start of the test.

These pellets were presented to white laboratory mice which were kept together for 24 hours, without additional feed. Water was available ad libidum. The remainders of the pellets were again dried after the end of the test, and weighed.

The measure of the repellent action is the re-weighed residual amount, expressed as a percentage of the amount originally employed. 100% repellent action means that nothing whatsoever had been eaten from the pellets.

The active compounds, the number of the tests and the results can be seen from Table 5.

EXAMPLE 7

Game preserve test/black-tailed deer
Test animal: black-tailed deer (*Odocoileus columbianus*)

To produce a suitable preparation of active compound, 6 parts by weight of active compound and 10 parts by weight of a copolymer of methacrylic acid methyl ester and butadiene as the adhesion agent were dispersed in 84 parts by weight of water. Two year old Douglas fir seedlings (*Pseudotsuga taxifolia*), 18 – 30 cm high, were entirely immersed in the preparation of the active compound. After drying, the plants were entirely covered with a thin layer of the adhesive, containing active compound, and were planted in a game preserve of size 1.01 ha. 10 test plots were laid out within the preserve, in each of which plots stood 20 seedlings which had been treated with active compound, 20 seedlings which had been treated with the standard agent tetramethylthiuram disulphide (TMTD) and 20 seedlings which were untreated and served as controls.

The game preserve was now populated with 10 black-tailed deer. The test ran until intermediate checks showed that the untreated seedlings had been gnawed to the extent of 60 to 80%. Thereafter the average degree of gnawing was determined. 100% denotes that all seedlings had been gnawed and 0 denotes that none of the seedlings had been gnawed.

The active compounds, dosages, number of treated seedlings and average degrees of gnawing can be seen from Table 7.

Table 7

| Active compound | game preserve test/black-tailed deer | | | |
| --- | --- | --- | --- | --- |
| | | Dosage of the active compound in treatment medium in % by weight | Number of treated seedlings | Average degree of gnawing |
| tetramethylthiuram disulfide (known) | (E) | 6 | 200 | 47.91 |
| untreated control | — | | 200 | 74.87 |
| 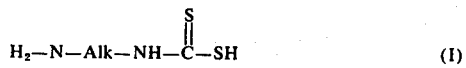 | (1) | 6 | 200 | 20.75 |

It will be appreciated that the instant specification and examples are set forth by way of illustration and not limitation, and that various modifications and changes may be made without departing from the spirit and scope of the present invention.

What is claimed is:

1. A method of repelling rodents or ruminants comprising applying to a rodent or ruminant habitat a repellent amount of a compound of the formula $$H_2-N-Alk-NH-\overset{S}{\underset{\|}{C}}-SH \qquad (I)$$

in which
Alk is an alkylene radical of 2 to 6 carbon atoms.

2. The method according to claim 1 in which the compound is an ω-aminoalkyl-dithiocarbamic acid.

3. The method of claim 1 in which said compound is 2-aminoethyl-dithiocarbamic acid.

4. The method of claim 1 in which said compound is 4-aminobutyl-dithiocarbamic acid.

5. The method of claim 1 in which said compound is 6-aminohexyl-dithiocarbamic acid.

* * * * *